United States Patent
Schroven et al.

(10) Patent No.: US 9,896,470 B2
(45) Date of Patent: *Feb. 20, 2018

(54) ENHANCING THE STABILITY AND PURITY AND INCREASING THE BIOAVAILABILITY OF HUMAN MILK OLIGOSACCHARIDES OR PRECURSORS OR BLENDS THEREOF

(71) Applicant: Glycom A/S, Hørsholm (DK)

(72) Inventors: Andreas Schroven, Barssel (DE); Gyula Dekany, Sinnamon Park (AU); Peter Erdmann, Bern (CH); Andrea Schwarz, Bern (CH)

(73) Assignee: Glycom A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,256

(22) PCT Filed: Jun. 14, 2013

(86) PCT No.: PCT/DK2013/050197
§ 371 (c)(1),
(2) Date: Dec. 11, 2014

(87) PCT Pub. No.: WO2013/185780
PCT Pub. Date: Dec. 19, 2013

(65) Prior Publication Data
US 2015/0183814 A1    Jul. 2, 2015

(30) Foreign Application Priority Data

Jun. 14, 2012 (DK) .................................. 2012 70329

(51) Int. Cl.
| | | |
|---|---|---|
| C07H 1/06 | (2006.01) |
| C07H 3/06 | (2006.01) |
| A61K 31/702 | (2006.01) |
| A23L 29/30 | (2016.01) |
| A23L 33/00 | (2016.01) |
| A23L 33/10 | (2016.01) |

(52) U.S. Cl.
CPC .............. *C07H 1/06* (2013.01); *A23L 29/30* (2016.08); *A23L 33/10* (2016.08); *A23L 33/40* (2016.08); *A61K 31/702* (2013.01); *C07H 3/06* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| 2007/0298116 A1 | 12/2007 | Bechtold-Peters et al. | |
| 2011/0268680 A1 | 11/2011 | Zhong | |
| 2014/0087021 A1* | 3/2014 | Berrocal | A23L 1/296 426/2 |

FOREIGN PATENT DOCUMENTS

| CN | 101781371 | 7/2010 |
| CN | 102154163 | 8/2011 |
| EP | 0529748 | 12/1992 |
| NZ | 240002 | 11/1993 |
| WO | WO2006087391 | 8/2006 |
| WO | WO2010115934 | 10/2010 |
| WO | WO2010115935 | 10/2010 |
| WO | WO2011100979 | 8/2011 |
| WO | WO2011100980 | 8/2011 |
| WO | WO2011150939 | 12/2011 |
| WO | WO2012007585 | 1/2012 |
| WO | WO2012155916 | 11/2012 |

OTHER PUBLICATIONS

Buchi, best@buchi, Information Bulletin, www.buchi.com, No. 57/2010.*
Roos, Le Lait, 2002, 82(4), pp. 475-484.*
FDA, Powdered Infant Formula: An Overview of Manufacturing Processes, internet article, obtained from Internet Archive, Mar. 2010.*
Abbas, K. et al, "The Significance of Glass Transition Temperature in Processing of Selected Fried Food Products: A Review", Modern Applied Science, 4:5:3-21, See whole document, in particular abstract. (2010).
Elamin, A. et al, "The use of amorphous model substances to study mechanically activated materials in the solid state", International Journal of Pharmaceutics, (1995), vol. 119, pp. 25-36, (1995), See abstract and p. 26, right column, "2.2 Methods"; p. 31, left column, lines 1-4 and p. 31, right column, tines 11-15 from the foot).
Duarte, I. et al, "Overcoming Poor Bioavailability Through Amorphous Solid Dispersions", Industrial Pharmacy, Issue 30, pp. 4-6, (2011).
Langrish, T. et al, "Crystallization Rates for Amorphous Sucrose and Lactose Powders from Spray Drying: A Comparison", Drying Technology, vol. 27, pp. 606-616, (2009), See p. 607-608 Materials; p. 608, right column, "sorption test" and Table 2, p. 608).
Paterson, A. et al, "Measurement of the effective diffusion coefficient of water in spray dried amorphous lactose particles", Procedia Food Science, vol. I, pp. 1924-1931, (2011), See p. 1925, lines 4-9 from the foot.

(Continued)

Primary Examiner — Layla D Berry
(74) Attorney, Agent, or Firm — Neal, Gerber & Eisenberg LLP

(57) ABSTRACT

The present application discloses a method for enhancing the stability of a human milk oligosaccharide (HMO) or a HMO precursor or a HMO blend when stored for extended periods at temperatures above 25° C. by spray-drying an aqueous solution of the HMO or HMO precursor to remove at least 90% of the water and providing a HMO or a HMO precursor or a HMO blend with a specific glass transition temperature. Also disclosed is a method for removing organic solvent residues from a human milk oligosaccharide (HMO) or a HMO precursor or a HMO blend by spray drying. Also disclosed is a method of enhancing the bioavailability of a human milk oligosaccharide (HMO) or a HMO precursor or a HMO blend by spray drying.

17 Claims, No Drawings

(56) References Cited

OTHER PUBLICATIONS

Bitz, C. et al, "Influence of the preparation method on residual solvents in biodegradable microspheres", International Journal of Pharmaceutics, vol. 131, pp. 171-181, (1996).

Patel, R. et al, "Spray drying technology: An overview", Indian Journal of Science and Technology, 2:10:44-47, ISSN: 0974-6846, (Oct. 2009).

Grodowska, K. et al, "Organic solvents in the pharmaceutical industry", Acta Poloniac Pharmaceutica—Drug Research, Polish Pharmaceutical Society, Krakow, Poland, vol. 67, pp. 3-12, (2010).

Urashima, T. et al, "Milk Oligosaccharides", Nutrition and Diet Research Progress, Nova Biomedical Books, New York, (2011), ISBN:978-61122-831-1.

\* cited by examiner

ENHANCING THE STABILITY AND PURITY AND INCREASING THE BIOAVAILABILITY OF HUMAN MILK OLIGOSACCHARIDES OR PRECURSORS OR BLENDS THEREOF

CROSS REFERENCE TO RELATED APPLICATIONS

This is a national stage filing in accordance with 35 U.S.C. § 371 of PCT/DK2013/050197, filed Jun. 14, 2013, which claims the benefit of the priority of Denmark Patent Application No. PA 2012 70329, filed Jun. 14, 2012; the contents of each are incorporated herein by reference.

FIELD OF THE INVENTION

The present invention relates to a method of purifying human milk oligosaccharides (HMOs) and precursors and derivatives thereof, particularly as produced by catalytic hydrogenolysis.

BACKGROUND OF THE INVENTION

Human milk oligosaccharides (HMOs) have become of great interest in the past few years due to their important functions in human development. To date, the structures of at least 115 HMOs have been determined (see Urashima et al.: Milk Oligosaccharides, Nova Biomedical Books, New York, 2011, ISBN: 978-1-61122-831-1), and considerably more are probably present in human milk. The thirteen core structures identified to date, for the 115 HMOs, are listed in Table 1:

TABLE 1

| \multicolumn{2}{c}{Core HMO structures} | |
| No | Core name | Core structure |
| --- | --- | --- |
| 1 | lactose (Lac) | Galβ1-4Glc |
| 2 | lacto-N-tetraose (LNT) | Galβ1-3GlcNAcβ1-3Galβ1-4Glc |
| 3 | lacto-N-neotetraose (LNnT) | Galβ1-4GlcNAcβ1-3Galβ1-4Glc |
| 4 | lacto-N-hexaose (LNH) | Galβ1-3GlcNAcβ1-3(Galβ1-4GlcNAcβ1-6)Galβ1-4Glc |
| 5 | lacto-N-neohexaose (LNnH) | Galβ1-4GlcNAcβ1-3(Galβ1-4GlcNAcβ1-6)Galβ1-4Glc |
| 6 | para-lacto-N-hexaose (para-LNH) | Galβ1-3GlcNAcβ1-3Galβ1-4GlcNAcβ1-3Galβ1-4Glc |
| 7 | para-lacto-N-neohexaose (para-LNnH) | Galβ1-4GlcNAcβ1-3Galβ1-4GlcNAcβ1-3Galβ1-4Glc |
| 8 | lacto-N-octaose (LNO) | Galβ1-3GlcNAcβ1-3(Galβ1-4GlcNAcβ1-3Galβ1-4GlcNAcβ1-6)Galβ1-4Glc |
| 9 | lacto-N-neooctaose (LNnO) | Galβ1-4GlcNAcβ1-3(Galβ1-3GlcNAcβ1-3Galβ1-4GlcNAcβ1-6)Galβ1-4Glc |
| 10 | iso-lacto-N-octaose (iso-LNO) | Galβ1-3GlcNAcβ1-3(Galβ1-3GlcNAcβ1-3Galβ1-4GlcNAcβ1-6)Galβ1-4Glc |
| 11 | para-lacto-N-octaose (para-LNO) | Galβ1-3GlcNAcβ1-3Galβ1-4GlcNAcβ1-3Galβ1-4GlcNAcβ1-3Galβ1-4Glc |
| 12 | lacto-N-neodecaose (LNnD) | Galβ1-3GlcNAcβ1-3[Galβ1-4GlcNAcβ1-3(Galβ1-4GlcNAcβ1-6)Galβ1-4GlcNAcβ1-6]Galβ1-4Glc |
| 13 | lacto-N-decaose (LND) | Galβ1-3GlcNAcβ1-3[Galβ1-3GlcNAcβ1-3(Galβ1-4GlcNAcβ1-6)Galβ1-4GlcNAcβ1-6]Galβ1-4Glc |

Low cost ways have been sought for making industrial quantities of as many as possible of the HMOs, so that their uses in nutritional and therapeutic formulations for infants, as well as as possibly children and adults, could be discovered, developed and exploited by researchers worldwide. A few HMOs have recently been chemically synthesized in high yields, for example, by hydrogenating their protected benzylated derivatives after removing other protecting groups from such protected derivatives and then crystallizing them from organic solvents. See WO 2010/115935 (2'-O-fucosyllactose or 2'-FL), WO 2011/100980 (lacto-N-neotetraose or LNnT), WO 2012/155916 (lacto-N-tetraose or LNT), WO 2011/100979 (6'-O-sialyllactose or 6'-SL) and WO 2012/007585 (various HMOs), and WO 2011/150939 (2'-FL polymorphs).

However, the relatively pure, crystalline HMOs, synthesized according to the above-mentioned methods may still be contaminated with small residues, i.e., about 1000 to 2000 ppm, but at least 100 ppm, of one or more of the following: i) toluene from the benzyl glycoside protecting group removed from their protected precursors by hydrogenolysis and ii) protic solvents such as $C_1$-$C_6$ alcohols used as the solvent or co-solvent with water in the hydrogenolysis step and/or used as the solvent or co-solvent in a subsequent crystallization or recrystallization of the HMOs. In order to use the HMOs in nutritional and therapeutic formulations for mammals, especially for humans, particularly for infants, it has been necessary to substantially reduce such residual contaminants, e.g., down to 500 ppm or less, preferably down to 100 ppm or less. Heretofore, this has required additional costly processing of the HMOs.

Accordingly, it is an object of the present invention to provide a method for removing, or reducing substantially the amount and/or concentration of organic solvent residues in and/or on HMOs, HMO precursors and blends, particularly blends of several HMOs and/or HMO precursors.

Moreover, crystalline HMOs have shown to be relatively unstable when stored for extended periods without refrigeration. They have tended to melt and thereby become sticky and form agglomerations.

Accordingly, it is also an object of the present invention to provide a method for enhancing the stability of HMOs, especially HMO blends, so that they can be stored for extended periods without refrigeration, for example at temperatures of up to 30° C. or even higher, preferably up to 40° C. or even higher.

Moreover, crystalline HMOs, as well as their precursors, and blends, have been relatively difficult to dissolve in water, so that they can be readily mixed with other active ingredients and suitable adjuvants for making liquid and powder, nutritional and therapeutic formulations. In addition, they have dissolved relatively slowly in the aqueous acid in the stomachs of mammals, particularly humans, quite particularly infants, which has reduced their bioavailability for the mammals.

Accordingly, it is a further object of the present invention to provide a method for enhancing the ability of HMOs, as well as their precursors, and blends, to dissolve in water and in the stomach acid of mammals.

Recently, CN 102154163 A disclosed spray-drying of an HMO, namely 3'-SL, produced by fermentation.

SUMMARY OF THE INVENTION

The first aspect of this invention relates to a method for enhancing the stability of a human milk oligosaccharide (HMO) or HMO precursor or blend when stored for extended periods at temperatures above 25° C., comprising the steps of:
a) providing the HMO or HMO precursor or blend in an aqueous solution, preferably at about its maximum concentration, especially at a concentration of at least about 30-60 wt %, particularly at least about 40-50 wt %, and
b) then spray-drying the aqueous solution to remove substantially all, preferably at least about 90%, particularly at least about 95%, of the water and provide the HMO or HMO precursor or blend with a higher glass transition temperature ($T_g$) that is at least 40° C., preferably at least 50° C., more preferably at least 60° C., even more preferably at least 70° C., particularly at least 80° C.

An embodiment of this first aspect of the invention relates to spray-drying the aqueous solution at about 130-210° C., preferably 140 to 180° C., particularly 140 to 160° C., to provide a water content of about 8-10% or lower, preferably about 4-6% or lower, and thereby increase its $T_g$ to about 40° C. or higher, preferably to about 50° C. or higher, more preferably to about 60° C. or higher, even more preferably to about 70° C. or higher, particularly to about 80° C. or higher.

The second aspect of the invention relates to a human milk oligosaccharide (HMO) or HMO precursor or blend, being present in an amorphous form and having a glass transition temperature ($T_g$) of at least 40° C., preferably at least 50° C., more preferably at least 60° C., even more preferably at least 70° C., particularly at least 80° C.

An embodiment of the second aspect relates to a human milk oligosaccharide (HMO), preferably that selected from the group consisting of LNT, LNnT, LNH, LNnH, para-LNH, para-LNnH, 2'-FL, 3-FL, DFL, LNFP I, LNFP II, LNFP III, LNFP V, F-LNnH, DF-LNH I, DF-LNH II, DF-LNH I, DF-para-LNH, DF-para-LNnH, 3'-SL, 6'-SL, FSL, F-LST a, F-LST b, F-LST c, LST a, LST b, LST c and DS-LNT, more preferably from LNT, LNnT, 2'-FL, 3-FL, DFL, LNFP I, 3'-SL, 6'-SL, FSL, LST a, and DS-LNT, even more preferably from LNT, LNnT, 2'-FL, 3-FL, 3'-SL and 6'-SL, particularly from LNnT, 2'-FL and 6'-SL, being present in an amorphous form and having a glass transition temperature ($T_g$) of at least 40° C.

Another embodiment of this second aspect relates to a human milk oligosaccharide (HMO) selected from LNT, LNnT, 2'-FL, 3-FL, DFL, LNFP I, 3'-SL, 6'-SL, FSL, LST a, and DS-LNT, even more preferably from LNT, LNnT, 2'-FL, 3-FL, 3'-SL and 6'-SL, particularly from LNnT, 2'-FL and 6'-SL, being present in an amorphous form and having a glass transition temperature ($T_g$) of at least 50° C., preferably at least 60° C., more preferably at least 70° C., particularly at least 80° C.

Yet another embodiment of the second aspect of the invention relates to a blend comprising 2 or more, preferably 5 or more HMOs and/or HMO precursors being present in an amorphous form and having a glass transition temperature ($T_g$) of at least 50° C., preferably at least 60° C.

A further embodiment of the second aspect of the invention relates to a blend comprising 2 or more, preferably 5 or more HMOs selected from LNT, LNnT, 2'-FL, 3-FL, DFL, LNFP I, 3'-SL, 6'-SL, FSL, LST a, and DS-LNT, preferably from LNT, LNnT, 2'-FL, 3-FL, 3'-SL and 6'-SL, being present in an amorphous form and having a glass transition temperature ($T_g$) of at least 60° C.

The third aspect of this invention relates to a method for removing, or at least reducing substantially, an amount or concentration of a residue of an organic solvent in or on a human milk oligosaccharide (HMO) or a precursor of an HMO or an HMO blend, particularly in or on a crystalline HMO or HMO precursor or blend, comprising the steps of:
a) providing the HMO or HMO precursor or blend in an aqueous solution, preferably at about its maximum concentration, especially at a concentration of at least about 30-60 wt %, particularly at least about 40-50 wt %; and
b) then spray drying the aqueous solution to remove substantially all, preferably at least about 90%, particularly at least about 95%, of the water and remove substantially all, preferably at least about 75%, particularly at least about 85%, of the organic solvent residue from the HMO or HMO precursor or blend.

An embodiment of this third aspect of the invention relates to using the method for removing or reducing the organic solvent residue from an HMO or HMO precursor or blend that has been made by a catalytic hydrogenolysis of a protected derivative of the HMO or HMO precursor or blend, which protected derivative had a protecting group removable by catalytic hydrogenolysis, preferably a benzyl group. In a preferred embodiment, the organic solvent residue comprises the hydrogenolized protecting group, that is toluene or a substituted toluene, preferably toluene.

Another embodiment of the third aspect of the invention relates to using the method for removing or reducing the organic solvent residue from an HMO or HMO precursor or blend that has been made by a catalytic hydrogenolysis of a protected derivative of the HMO or HMO precursor or blend in a protic solvent, preferably a lower alkanol or aqueous lower alkanol solvent. In a preferred embodiment, the organic solvent residue comprises a residue of the protic solvent, preferably of a lower alkanol, particularly methanol.

Yet another embodiment of the third aspect of the invention relates to using the method for removing or reducing the residues of two or more organic solvents from an HMO or HMO precursor or blend that has been made by a catalytic hydrogenolysis, in a protic solvent, preferably a lower alkanol or aqueous lower alkanol solvent, of a protected derivative of the HMO or HMO precursor or blend which protected derivative has a protecting group removable by catalytic hydrogenolysis, preferably a benzyl group. In a preferred embodiment, one organic solvent residue comprises the hydrogenolized protecting group, that is toluene or a substituted toluene, preferably toluene, and another organic solvent residue comprises a residue of the protic solvent, preferably of a lower alkanol, particularly methanol.

A further embodiment of the third aspect of the invention relates to using the method for removing or reducing one or more organic solvent residues from a blend or mixture of 2 or more, preferably 5 or more HMOs and/or HMO precursors, which have been separately crystallized from one or more organic solvents.

A still further embodiment of the third aspect of the invention relates to using the method for removing an organic solvent residue from an HMO or HMO precursor or derivative or blend that has been crystallized from an organic solvent. In one embodiment of this aspect, the organic solvent residue comprises a lower alkanol, preferably methanol.

The fourth aspect of this invention relates to a method for enhancing the bioavailability for mammals, particularly humans, quite particularly infants, of an HMO or HMO precursor or an HMO blend, comprising the steps of:
a) providing the HMO or HMO precursor or blend in an aqueous solution, preferably at about its maximum concentration, especially at a concentration of at least about 30-60 wt %, particularly at least about 40-50 wt %; and
b) then spray-drying the aqueous solution to remove substantially all, preferably at least about 90%, particularly at least about 95%, of the water and provide the HMO or HMO precursor or derivative or blend with an amorphous physical state.

DETAILED DESCRIPTION OF THE INVENTION

In accordance with this invention, an aqueous solution of a human milk oligosaccharide (HMO) or its precursor or a blend of HMOs and/or HMO precursors is spray-dried, preferably in a single spray-drying step, to:
remove, from it, substantially all, preferably at least about 90%, particularly at least about 95%, of the water; and thereby
remove, from it, substantially all, preferably at least about 75%, especially at least about 85%, of a residue of an organic solvent, preferably a lower alkanol, more preferably methanol; and also
enhance its stability when stored for extended periods at temperatures above 25° C.; and/or also
enhance its bioavailability for mammals, particularly humans, quite particularly infants.

Also in this invention, the term "protecting group removable by catalytic hydrogenolysis" refers to a group, whose C—O bond is cleaved by addition of hydrogen in the presence of a hydrogenolysis catalyst. The hydrogenolysis catalyst is used in the presence of hydrogen gas under pressure. The hydrogenolysis catalyst can be for example palladium, Raney nickel, palladium on charcoal or palladium black or another appropriate metal catalyst known for use in hydrogenolysis. The hydrogenolysis results in the regeneration of the OH-group that had been protected. The protecting groups of this type are known (see e.g. P. G. M. Wuts and T. W. Greene: *Protective Groups in Organic Synthesis*, John Wiley & Sons (2007)). Suitable protecting groups include benzyl, diphenylmethyl (benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). A particularly preferred protecting group is benzyl optionally substituted with one or more groups selected from alkyl or halogen. More preferably, the protecting group is selected from unsubstituted benzyl, 4-chlorobenzyl and 4-methylbenzyl. These particularly preferred and more preferable protecting groups have the advantage that the by-products of the hydrogenolysis (as the hydrogenolized protecting groups) are exclusively toluene or substituted toluene. Such by-products can easily be removed even in multi ton scales from water soluble oligosaccharide products via evaporation and/or extraction processes.

Further in this invention, the term "lower alkanol" preferably means a hydroxy- or dihydroxy-alkanol having 1 to 6 carbon atoms, such as methanol, ethanol, n-propanol, i-propanol, ethylene glycol, di-ethylene glycol, 1,2-propanediol, 1,3-propanediol, butanol and an i-hexanol, especially a "$C_1$-$C_4$ alcohol", such as methanol, ethanol, isopropanol, 1,2-propanediol and t-butanol, particularly methanol.

Also in this invention, the term "HMO" refers to tri-, tetra- and oligosaccharides found in mother's milk (see Urashima et al.: Milk Oligosaccharides, Nova Biomedical Books, New York, 2011, ISBN: 978-1-61122-831-1). Preferably, an HMO is selected from the group consisting of LNT, LNnT, LNH, LNnH, para-LNH, para-LNnH, 2'-FL, 3-FL, DFL, LNFP I, LNFP II, LNFP III, LNFP V, F-LNnH, DF-LNH I, DF-LNH II, DF-LNH I, DF-para-LNH, DF-para-LNnH, 3'-SL, 6'-SL, FSL, F-LST a, F-LST b, F-LST c, LST a, LST b, LST c and DS-LNT, more preferably from LNT, LNnT, 2'-FL, 3-FL, DFL, LNFP I, 3'-SL, 6'-SL, FSL, LST a, and DS-LNT, even more preferably from LNT, LNnT, 2'-FL, 3-FL, 3'-SL and 6'-SL, particularly from LNnT, 2'-FL and 6'-SL.

Yet in this invention, an HMO precursor preferably means mono-, di- and trisaccharides that are the parts of HMOs, that is glucose, galactose, N-acetyl-glucosamine, fucose, sialic acid, lactose, lacto-N-biose (Galβ1-3GlcNAc), N-acetyl-lactosamine (Galβ1-4GlcNAc) and lacto-N-triose (GlcNAcβ1-3Galβ1-4Glc). Preferred HMO precursors are selected from the group consisting of fucose, sialic acid, lacto-N-biose, N-acetyl-lactosamine and lacto-N-triose.

Also in this invention, the term "blend" or "HMO blend" refers to a mixture of two or more, preferably 5 or more HMOs and/or HMO precursors. Preferably, the blend consists of two or more, preferably 5 or more HMOs selected from LNT, LNnT, LNH, LNnH, para-LNH, para-LNnH, 2'-FL, 3-FL, DFL, LNFP I, LNFP II, LNFP III, LNFP V, F-LNnH, DF-LNH I, DF-LNH II, DF-LNH I, DF-para-LNH, DF-para-LNnH, 3'-SL, 6'-SL, FSL, F-LST a, F-LST b, F-LST c, LST a, LST b, LST c and DS-LNT, more preferably from LNT, LNnT, 2'-FL, 3-FL, DFL, LNFP I, 3'-SL, 6'-SL, FSL, LST a, and DS-LNT, even more preferably from LNT, LNnT, 2'-FL, 3-FL, 3'-SL and 6'-SL.

In carrying out this invention, a protected derivative of an HMO or HMO precursor or HMO blend, which protected derivative has a protecting group removable by catalytic hydrogenolysis, preferably a benzyl group, can be catalytically hydrogenolized in a conventional manner in a protic solvent, preferably a lower alkanol or aqueous lower alkanol solvent, or in an aqueous solution with a protic solvent, to yield a solution of the HMO or HMO precursor or blend. See WO 2012/007585 which is incorporated herein by reference. The resulting solution—containing organic solvent residues often of about 1000 to 2000 ppm of toluene or a substituted toluene produced during the hydrogenolysis and often about 1000 to 2000 ppm of the protic solvent used in the hydrogenolysis—is preferably heated to partially evaporate the protic solvent, to concentrate the solution, and also to partially evaporate the toluene or substituted toluene and the protic solvent. Preferably, the resulting aqueous solution is then diluted one or more times with water and concentrated again to substantially reduce each of such organic solvent residues. In this regard, the resulting aqueous solution preferably has a protic solvent content of no more than about 500 ppm, especially no more than about 100 ppm, particularly no more than about 50 ppm, and a toluene or a substituted toluene content of no more than about 200 ppm, preferably no more than about 50 ppm, particularly no more than about 20 ppm. Moreover, the resulting aqueous solution has a concentration of an HMO or HMO precursor or HMO blend of about 10-50 wt %, preferably about 20-40 wt %, particularly about 25-35 wt %.

Alternatively in carrying out this invention, a dry HMO or HMO precursor or blend, preferably in crystalline form, can be dissolved in a conventional manner in water. The water is preferably heated somewhat, for example up to about 40-50° C., to promote the dissolution of the HMO or HMO precursor or blend in the resulting aqueous solution, preferably up to its maximum concentration (e.g. about 10-50 wt %), especially to a concentration of about 20-40 wt %, particularly about 25-35 wt %.

The resulting aqueous solution can then be spray-dried in a conventional manner with hot air or hot inert gas, preferably hot air, at about 130-210° C., preferably 140 to 180° C., particularly 140 to 160° C. to produce a substantially dry, amorphous, free-flowing powder of the HMO or HMO precursor or blend. In this regard, any conventional spray-drying apparatus can be used, such as a co-current or a multiple effect spray-dryer, preferably a two-stage spray dryer (with a fluid bed attachment). Likewise, the choice of the atomizer or spray nozzle in the spray-dryer is not considered critical, and any common rotary disk or high pressure swirl nozzle can be suitably utilized.

Preferably, a spray-dried powder of the HMO or HMO precursor or blend is obtained with substantially all, preferably at least about 90%, particularly at least about 95%, of its water content removed and substantially all, especially at least about 75%, particularly at least about 85%, of its organic solvent residues, particularly of toluene or substituted toluene, preferably toluene, and/or of a lower alkanol, preferably methanol, that had been present in the feed solution before spray-drying, removed. The glass transition temperature ($T_g$) of the spray-dried powder is a function of its water content, but a water content of about 8-10% or less, preferably about 4-6% or less, can provide a $T_g$ of at least 40° C., preferably of at least 50° C., more preferably of at least 60° C., even more preferably of at least 70° C., particularly of at least 80° C. Such a $T_g$ can be readily achieved by spray-drying the HMO or HMO precursor or blend at about 130-210° C., preferably 140 to 180° C., particularly 140 to 160° C. Advantageously, a $T_g$ can be increased to about 80° C. or higher when an HMO selected from LNT, LNnT, 2'-FL, 3-FL, DFL, LNFP I, 3'-SL, 6'-SL, FSL, LST a and DS-LNT, preferably from LNT, LNnT, 2'-FL, 3-FL, 3'-SL and 6'-SL, more preferably from LNnT, 2'-FL and 6'-SL, is spray-dried. Also advantageously, in case of spray-drying an HMO blend comprising 2 or more HMOs and/or HMO precursors, preferably 5 or more HMOs selected from the group consisting of LNT, LNnT, 2'-FL, 3-FL, DFL, LNFP I, 3'-SL, 6'-SL, FSL, LST a and DS-LNT, even more preferably from LNT, LNnT, 2'-FL, 3-FL, 3'-SL and 6'-SL, a $T_g$ can be increased to about 60° C. or higher. The resulting amorphous powder of an HMO or HMO precursor or blend with a $T_g$ of at least 60° C. can be stored at max. about 50° C., and with a $T_g$ of at least 80° C. can be stored at max. about 60° C., and such powder can be stored for prolonged periods without significant change in its composition and without significant decomposition while it remains amorphous.

Also preferably, a spray-dried powder of the HMO or HMO precursor or blend obtained by the method of this invention contains only small amounts or concentration of organic solvent residues. Some HMOs, blends or HMO precursors can have a great affinity to adsorbe organic solvents that can only be removed partially by conventional drying methods. Crystallized fucosylated HMOs, particularly 2'-FL, strongly bind to lower alcohols, especially methanol, the amount of which cannot be reduced below a certain value. This can prevent the use of such HMOs in food and pharmaceutical applications. This problem can be overcome by spray-drying, rather than crystallizing, the HMO or HMO precursor or blend, especially 2'-FL, having a high organic solvent residue concentration after its chemical or chemo-enzymatic synthesis.

The amorphous powder of an HMO or HMO precursor or blend obtained by the method of the invention can be beneficially utilized for making nutritional formulations (such as food, drink or feed), food supplements, digestive health functional foods or other consumable products, intended for use with infants, children, adults or seniors.

Accordingly, a further aspect of the invention relates to a pharmaceutical composition for treating infants, children, adults and/or seniors and particularly subjects having specialized needs (e.g., suffering from metabolic disorders), comprising the amorphous powder of an HMO or HMO precursor or blend according to the second aspect. The amorphous powder of an HMO or HMO precursor or blend according to the second aspect can be added to a pharmaceutically acceptable carriers such as conventional additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. When the amorphous powder of an HMO or HMO precursor or blend according to the second aspect is added to the pharmaceutically acceptable carriers, a dosage in the form of for example, but not limited to tablets, powders, granules, suspensions, emulsions, infusions, capsules, injections, liquids, elixirs, extracts and tincture can be made. To the above formulas, if needed, probiotics, e.g. lacto bacteria, *Bifidobacterium* species, prebiotics such as fructooligosaccharides and galactooligosaccharides, proteins from casein, soybean, whey or skim milk, carbohydrates such as lactose, saccharose, maltodextrin, starch or mixtures thereof, lipids (e.g. palm olein, sunflower oil, safflower oil) and vitamins and minerals essential in a daily diet can also be further added.

Pharmaceutical compositions comprising the amorphous powder of an HMO or HMO precursor or blend according to the second aspect can be manufactured by means of any usual manner known in the art, e.g. described in the most recent edition of Remington's Pharmaceutical Sciences, a standard reference text in the field.

An even further aspect of the invention is a nutritional formulation, such as food, drink or feed, containing the amorphous powder of an HMO or HMO precursor or blend according to the second aspect and conventional edible micronutrients, vitamins and minerals. The amounts of such ingredients can vary depending on whether the consumable product is intended for use with infants, children, adults, seniors or subjects having specialized needs (e.g., suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolyzed cornstarch, etc.) and proteins from casein, soy-bean, whey or skim milk, or hydrolysates of these proteins, but protein from other source (either intact or hydrolysed) can be used as well. Vitamins can be chosen such as vitamin A, B1, B2, B5, B6, B12, C, D, E, H, K, folic acid, inositol and nicotinic acid. The nutritional formulation can contain the following minerals and trace elements: Ca, P, K, Na, Cl, Mg, Mn, Fe, Cu, Zn, Se, Cr or I. Furthermore additional probiotics can be added, e.g. lacto bacteria, *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet can also be further added.

In a preferred embodiment, the nutritional formulation comprising the amorphous powder of an HMO or HMO precursor or blend according to the second aspect can be a food supplement. Such a food supplement preferably contains ingredients as defined for nutritional food above, e.g. vitamins, minerals, trace elements and other micronutrients, etc. The food supplement can be for example in the form of tablets, capsules, pastilles or a liquid. The supplement can contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc.

In another preferred embodiment, the nutritional formulation comprising the amorphous powder of an HMO or HMO precursor or blend according to the second aspect can be digestive health functional food as the administration of an HMO or HMO precursor or blend provides a beneficial effect on digestive health. Digestive health functional food is preferably a processed food used with intention to enhance and preserve digestive health by utilizing the mixture of oligosaccharides according to the present invention as physiologically functional ingredients or components in forms of tablet, capsule, powder, etc. Different terms such as dietary supplement, nutraceutical, designed food, health product can also be used to refer to digestive health functional food. The nutritional formulation comprising the amorphous powder of an HMO or HMO precursor or blend according to the second aspect can be prepared in any usual manner. For example, it can be prepared by admixing micronutrient components in appropriate proportions. Then the vitamins and minerals are added, but to avoid thermal degradation or decomposition heat sensitive vitamins can be added after homogenization. Lipophilic vitamins can be dissolved in the fat source before mixing. A liquid mixture is formed using water, whose temperature is preferably about between 50-80° C. to help dissolution or dispersal of the ingredients. The amorphous powder of an HMO or HMO precursor or blend according to the second aspect can be added at this stage. The resulting mixture is then homogenized by flash heating to about 80-150° C. by means of steam injection, heat exchanger or autoclave. This thermal treatment reduces significantly the bacterial loads as well. The hot mixture is then cooled rapidly to about 60-80° C. If needed, further homogenization can be carried out at this temperature under high pressure of about 2-30 MPa. After cooling heat sensitive constituents can be added at this stage, and the pH and the content of the solids are conveniently adjusted. The resulting mixture is then dried by conventional method such as spray drying or freeze drying to powder. Probiotics can be added at this point by dry-mixing.

EXAMPLES

The calorimetric experiments to determine the glass transition temperature of the amorphous samples were carried out using Perkin Elmer DSC-7 at a heating rate of 10° C./min; the samples (5-7 mg) were placed in open aluminium crucibles.

Example 1—Lacto-N-neotetraose (LNnT)

10 g (14.1 mmol) of the benzyl glycoside of LNnT (synthesized according to WO 2011/100980) were dissolved in 40 ml of water, 0.3 g of Pd—C and 80 μl of acetic acid were added, and the mixture was stirred at room temperature under $H_2$-atmosphere (approx. 40 bars) for 2 days. The reaction mixture was diluted with deionized water (10.0 ml), and the catalyst was filtered out. The mixture was concentrated to be 20 ml, then diluted with deionized water (30.0 ml) and concentrated to be 20 ml (22 g; 41% LNnT).

The concentrated solution was used for spray-drying on a Büchi Mini Spray Dryer B290 under the following conditions:

Inlet temperature: 160° C.
Outlet temperature: 75° C.
Aspirator: 38 m³/h
Compressed air: 600 l/h
Pump: 8 ml/min 96% of the methanol present in the feed solution was removed, and the spray-dried LNnT became an amorphous, non-sticky material displaying excellent shelf life below 40° C. storage temperature. $T_g$: 81.6° C. This suggests a storage temperature limit of around 60° C. for this LNnT material. Stability test after two months (40° C., rel. humidity 75%) showed no changes in the analytical data and powder X-ray diagram of the material.

Comparison of the amorphous spray-dried sample of LNnT obtained above with the crystalline sample of LNnT produced according to WO 2011/100980:

|  | MeOH (by GC) | water |
|---|---|---|
| amorphous spray-dried LNnT | 14 ppm | 3.2% |
| crystalline LNnT | 34 ppm | 8.5% |

The data show that significantly lower amounts of organic solvent residues and water can be found in the spray-dried amorphous material.

Example 2—2'-O-fucosyllactose (2'-FL)

(2-O-Benzyl-α-L-fucopyranosyl)-(1→2)-β-D-galactopyranosyl-(1→4)-D-glucose (synthesized according to WO 2010/115935) (10.0 g) was suspended in methanol (60 ml) and Pd/C (10%, 500 mg) suspended in methanol (5.0 ml) was added. The reaction mixture was then stirred under $H_2$ pressure (3 bar) for 40 h. The reaction mixture was diluted with deionized water (35 ml), and the catalyst was filtered off. The colourless solution was concentrated to be 30 ml, and then diluted with deionized water (35 ml) and concentrated to be 20 ml (22 g; 38% 2'-FL).

The concentrated solution was used for spray-drying on a Büchi Mini Spray Dryer B290 under following conditions:
Inlet temperature: 140° C.
Outlet temperature: 67° C.
Aspirator: 38 m³/h
Compressed air: 600 l/h
Pump: 8 ml/min 75% of the methanol present in the feed solution was removed. The spray-dried 2'-FL became an amorphous, non-sticky material containing 2.8% of water and displaying excellent shelf life below 40° C. storage temperature. $T_g$: 83.9° C. This suggests a storage temperature limit of around 60° C. for this 2'-FL material. Stability test after two months (40° C., rel. humidity 75%) showed no changes in the analytical data and powder X-ray diagram of the material.

Comparison of the amorphous spray-dried sample of 2'-FL obtained above with the crystalline sample of 2'-FL produced according to WO 2010/115935:

|  | MeOH (by GC) |
| --- | --- |
| amorphous spray-dried 2'-FL | 9 ppm |
| crystalline 2'-FL | 190 ppm |

The data show that significantly lower organic solvent residue can be found in the spray-dried amorphous material.

Example 3—6'-O-sialyllactose (6'-SL)

The sodium salt of the benzyl glycoside of 6'-SL (synthesized according to WO 2011/100979, 10.0 g) was solubilized in deionized water (15.0 ml), and 1.5 M aqueous HCl (2.20 m) was added followed by Pd/C (10%, 580 mg). The mixture was stirred under $H_2$ pressure (5 bar) for 20 h at 40° C. The catalyst was filtered off, and the filtrate was concentrated to be 10 ml. Deionized water (15.0 ml) was added, and the mixture was concentrated to be 15 ml (17 g; 52% 6'-SL). The solution was used for spray-drying on a Büchi Mini Spray Dryer B290 under the following conditions:
Inlet temperature: 140° C.
Outlet temperature: 57° C.
Aspirator: 38 m³/h
Compressed air: 600 l/h
Pump: 8 ml/min 84% of the methanol present in the feed solution was removed. The spray-dried 6'-SL became an amorphous, non-sticky material containing 6.9% of water and displaying excellent shelf life below 40° C. storage temperature. $T_g$: 84.0° C. This suggests a storage temperature limit of around 60° C. for this 6'-SL material.

Example 4—Sialic Acid (Neu5Ac)

Anhydrous Neu5Ac (5.00 g) was solubilized in deionized water (25.0 ml) by gentle warming. The solution was filtered warm, 2000 ppm methanol were added, and the solution was spray-dried immediately on a Büchi Mini Spray Dryer B290 under the following conditions:
Inlet temperature: 150° C.
Outlet temperature: 64° C.
Aspirator: 38 m³/h
Compressed air: 600 l/h
Pump: 8 ml/min 84% of the methanol present in the feed solution were removed under given conditions. The spray dried Neu5Ac became an amorphous, non sticky material displaying excellent shelf life below 40° C. storage temperature.

Example 5—HMO Blend

The following HMOs were dissolved by gentle warming in deionized water (9.50 ml):

| 2'-FL | 3.38 g |
| --- | --- |
| 3-FL | 0.87 g |
| LNT | 1.20 g |
| LNnT | 0.35 g |
| 3'-SL | 0.27 g |
| 6'-SL | 0.72 g |

2000 ppm methanol were added to the aqueous solution of HMOs, and the solution was spray-dried immediately on a Büchi Mini Spray Dryer B290 under the following conditions:
Inlet temperature: 150° C.
Outlet temperature: 63° C.
Aspirator: 38 m³/h
Compressed air: 600 l/h
Pump: 8 ml/min 73% of the methanol present in the solution was removed. The spray dried blend of HMOs became an amorphous, non-sticky material displaying excellent shelf life below 40° C. storage temperature. $T_g$: 63.6° C. This suggests a storage temperature limit of around 50° C. for the blend material.

The invention claimed is:

1. A method for preparing an amorphous form of a human milk oligosaccharide (HMO) or a HMO blend comprising: dissolving at least one synthetic HMO containing an organic solvent contaminant in water to form an aqueous solution; and spray-drying the aqueous solution to form an amorphous material, wherein the at least one synthetic HMO is selected from the group consisting of lacto-N-triose, lacto-N-tetraose (LNT), lacto-N-neotetraose (LNnT), lacto-N-hexaose (LNH), lacto-N-neohexaose (LNnH), para-lacto-N-hexaose (para-LNH), para-lacto-N-neohexaose (para-LNnH), 2-O-fucosyllactose (2'-FL), 3-O-fucosyllactose (3-FL), 2',3-di-O-fucosyllactose (DFL), lacto-N-fucopentaose I (LNFP I), lacto-N-fucopentaose II (LNFP II), lacto-N-fucopentaose II (LNFP III), lacto-N-fucopentaose V (LNFP V), fucosyl-lacto-N-neohexaose (F-LNnH), difucosyl-lacto-N-hexaose I (DF-LNH I), difucosyl-lacto-N-hexaose II (DF-LNH II), difucosyl-para-lacto-N-hexaose (DF-para-LNH), difucosyl-para-lacto-N-neohexaose (DF-para-LNnH), 3'-O-sialyllactose (3'-SL), 6'-O-sialyllactose (6'-SL), 3-O-fucosyl-3'-O-sialyllactose (FSL), sialyllacto-N-tetraose a (LST a), sialyllacto-N-tetraose b (LST b), sialyllacto-N-tetraose c (LST c), fucosyl-sialyllacto-N-tetraose a (F-LST a), fucosyl-sialyllacto-N-tetraose b (F-LST b), fucosyl-sialyllacto-N-tetraose c (F-LST c), and disialyllacto-N-tetraose (DS-LNT).

2. The method of claim 1, wherein the spray-drying results in the removal of at least about 90% of the water and the amorphous form of HMO or HMO blend has a glass transition temperature (Tg) that is at least 40° C.

3. The method of claim 2, wherein the spray-drying results in the removal of about 90-95% of the water.

4. The method of claim 1, wherein the at least one synthetic HMO is a crystalline HMO or HMO blend, wherein the stability of the amorphous form of the HMO or HMO blend has a greater stability than the crystalline HMO or HMO blend.

5. The method of claim 1, wherein the at least one synthetic HMO is selected from the group consisting of lacto-N-tetraose (LNT), lacto-N-neotetraose (LNnT), 2'-O-fucosyllactose (2'-FL), 3-O-fucosyllactose (3-FL), 2',3-di-O-fucosyllactose (DFL), lacto-N-fucopentaose I (LNFP I), 3'-O-sialyllactose (3'-SL), 6'-O-sialyllactose (6'-SL), 3-O-fucosyl-3'-O-sialyllactose (FSL), sialyllacto-N-tetraose a (LST a), and disialyllacto-N-tetraose (DS-LNT); and the amorphous form of HMO or HMO blend has a glass transition temperature (Tg) that is at least 80° C.

6. The method of claim 5, wherein the at least one synthetic HMO is selected from the group consisting of lacto-N-tetraose (LNT), lacto-N-neotetraose (LNnT), 2'-O-fucosyllactose (2'-FL), 3-O-fucosyllactose (3-FL), 3'-O-sialyllactose (3'-SL) and 6'-O-sialyllactose (6'-SL).

7. The method of claim 6, wherein the at least one synthetic HMO is selected from the group consisting of lacto-N-neotetraose (LNnT), 2'-O-fucosyllactose (2'-FL) and 6'-O-sialyllactose (6'-SL).

8. The method of claim 1, wherein the at least one synthetic HMO comprises two or more HMOs; and the amorphous form of HMO or HMO blend has a glass transition temperature (Tg) that is at least 60° C.

9. The method of claim 8, wherein the two or more HMOs are selected from the group consisting of lacto-N-tetraose (LNT), lacto-N-neotetraose (LNnT), 2'-O-fucosyllactose (2'-FL), 3-O-fucosyllactose (3-FL), 2',3-di-O-fucosyllactose (DFL), lacto-N-fucopentaose I (LNFP I), 3'-O-sialyllactose (3'-SL), 6'-O-sialyllactose (6'-SL), 3-O-fucosyl-3'O-sialyllactose (FSL), sialyllacto-N-tetraose a (LST a), and disialyllacto-N-tetraose (DS-LNT).

10. The method of claim 1, wherein the spray-drying results in the removal of at least 75% of the organic solvent contaminant.

11. The method of claim 1, wherein the at least one synthetic HMO is obtained via catalytic hydrogenolysis of a protected derivative of HMO; and the organic solvent contaminant is the hydrogenolized protecting group.

12. The method of claim 1, wherein the at least one synthetic HMO is obtained via catalytic hydrogenolysis of a protected derivative of HMO in a protic solvent; and the organic solvent contaminant is the protic solvent.

13. The method of claim 12, wherein the protic solvent is a lower alkanol.

14. The method of claim 1, wherein the at least one synthetic HMO comprises an HMO crystallized from an organic solvent.

15. The method of claim 12, wherein the HMO crystallized from an organic solvent is 2'-FL crystallized from a lower alkanol.

16. The method of claim 1, wherein the organic contaminant comprises methanol.

17. The method of claim 16, wherein the at least one synthetic HMO comprises 2'-O-fucosyllactose (2'-FL).

* * * * *